(12) United States Patent
Kristiansen et al.

(10) Patent No.: US 8,878,557 B2
(45) Date of Patent: Nov. 4, 2014

(54) ELECTRODE ARRANGEMENT FOR MONITORING A BED

(75) Inventors: Kjeld Kristiansen, Sønderborg (DK);
Allan H. Madsen, Sønderborg (DK)

(73) Assignee: Linak A/S, Nordborg (DK)

( * ) Notice: Subject to any disclaimer, the term of this patent is extended or adjusted under 35 U.S.C. 154(b) by 169 days.

(21) Appl. No.: 13/138,939

(22) PCT Filed: May 3, 2010

(86) PCT No.: PCT/DK2010/000059
§ 371 (c)(1),
(2), (4) Date: Nov. 14, 2011

(87) PCT Pub. No.: WO2010/124690
PCT Pub. Date: Nov. 4, 2010

(65) Prior Publication Data
US 2012/0038375 A1     Feb. 16, 2012

(30) Foreign Application Priority Data

May 1, 2009    (DK) ................................ 2009 00567

(51) Int. Cl.
| | | |
|---|---|---|
| G01R 23/20 | (2006.01) | |
| G01N 27/02 | (2006.01) | |
| G08B 21/20 | (2006.01) | |
| A61F 13/42 | (2006.01) | |
| G01N 27/12 | (2006.01) | |
| G01N 27/22 | (2006.01) | |

(52) U.S. Cl.
CPC .............. *G01N 27/121* (2013.01); *G08B 21/20* (2013.01); *A61F 13/42* (2013.01); *G01N 27/02* (2013.01); *G01N 27/223* (2013.01)
USPC ............................. 324/694; 324/620; 324/439

(58) Field of Classification Search
CPC ...... A61F 13/42; G01N 27/02; G01N 27/223; G01N 27/121; G08B 21/20
USPC ........................... 324/694, 620, 439; 340/620
See application file for complete search history.

(56) References Cited

U.S. PATENT DOCUMENTS 2,668,202 A * 2/1954 Kaplan ..................... 200/61.05
(Continued)

FOREIGN PATENT DOCUMENTS

| EP | 531247 | 3/1993 |
| EP | 586326 | 3/1994 |

(Continued)

OTHER PUBLICATIONS

English Abstract of EP531247.
English Abstract of EP586326.
English Abstract of EP647799.
English Abstract of EP662573.

*Primary Examiner* — Jermele M Hollington
*Assistant Examiner* — Farhana Hoque
(74) *Attorney, Agent, or Firm* — Dykema Gossett PLLC

(57) ABSTRACT

Equipment for indicating a bed-wetting in a bed comprising a bed-wetter sheet and a measuring- and control system. A measuring circuit is furnished to test whether the electrode in the bed-wetter sheet are intact, and afterwards to measure the conductivity in the normal state between the two from each other electrically isolated electrodes whereby the conductivity between the two electrodes will fall drastically by a bed-wetting, human fluids containing salt being spread on the sheet, and indicate the bed-wetting. The measuring circuit is furnished to as a part of a routine to enter into a resting state whereby the measurement is performed with a prearranged fixed time interval.

13 Claims, 2 Drawing Sheets

(56) References Cited

U.S. PATENT DOCUMENTS

| | | |
|---|---|---|
| 4,347,503 A | 8/1982 | Uycharu |
| 7,053,781 B1 * | 5/2006 | Haire et al. ................... 340/604 |
| 2010/0141281 A1 | 6/2010 | Johnsen |

FOREIGN PATENT DOCUMENTS

| | | | |
|---|---|---|---|
| EP | | 647799 | 4/1995 |
| EP | | 662573 | 7/1995 |
| NO | WO2009002180 | * | 12/2008 |

* cited by examiner

ELECTRODE ARRANGEMENT FOR MONITORING A BED

BACKGROUND OF THE INVENTION

1. Field of the Invention

The invention relates to equipment for a bed, especially a hospital or a care bed, and to a method for measuring whether a bed sheet is wet.

2. The Prior Art

The invention is primarily aimed at equipment for mounting on a bed for a safe indication whether the bed has become wet. The problem may arise if a person suffers from incontinency or profusely sweating. As far as children in the home as well as elderly persons within the nursing or hospital sector are concerned, it is desirable to achieve a safe indication whether the bed is wet. The desire originates in ethical and human respect, hygienic reasons, and for reasons of health. When a situation occurs where the bed has become wet, it is desirable to secure a safe and reliable indication for a fast relief of the problem, by warning the nursing staff that cleaning of the bed is required.

One kind of equipment for indicating whether a bed has become wet is a bed-wetter sheet. An example of a bed-wetter sheet is known from U.S. Pat. No. 2,668,202 (B. D. Kaplan). The bed-wetter sheet simply consists of a bed sheet with built in electrodes from which one can measure the mutual electrical isolation of the electrodes. The electrodes can be arranged parallel at one layer of the sheet, or be arranged at separate layers of the sheet. When the sheet is dry, the resistance will be high, whereas the presence of fluid will change the resistance between the electrodes, and especially when the fluid comprises salt, as it is the case where body fluids are concerned.

A measuring method for indication of a wet bed-wetter sheet is known form U.S. Pat. No. 4,347,503 (Otto A. Uyehara), whereby an electric circuit on a regular basis sends electric pulses to the electrodes of the bed-wetter sheet. When the sheet is wet, the impulses are lead through the sheet and will trigger a relay function in the form of a thyristor whereby an alarm is activated.

The bed-wetter sheet and the appliance for indication of a wet sheet is in a way an excellent solution, because the bed-wetter sheet can be washed and used again, besides it is also inexpensive and practical. The appliance for indicating when a sheet is wet is furthermore excellent, because voltage is not continuously impressed. The alarm function is also power-saving in that the pulses are sent only periodically, and in that way keeps the measuring equipment in a power-saving resting state most of the time.

However, the appliance has certain disadvantages as the system cannot indicate whether the electrodes are connected to the measuring circuit. The connection might be disconnected when the patient twitches the cables unintentionally, or when the nursing staff is carrying out their work with the patient. A faulty mounting of the electrodes when the equipment is mounted in the bed might also happen. Another faulty situation might happen when the electrodes in the sheet due to wear, by lapse of time or frequently washing are broken, and the lengths of the electrodes hereby have been diminished. It will thus not be possible to have an indication of that the bed is wet at a random point of the sheet, but only in the area where the electrodes are intact.

Another disadvantage of the equipment is that the measuring circuit is supplied from a battery which means that it has to be secured that the battery continuously is in a position to supply energy. The solution does not focus on personal safety or personal comfort either. The patient is in close contact with the wet area of the sheet which is why even a faint measuring current would bother the user. Especially when it comes to pulsing voltage, as stated in prior art, where the presence of a coil which is connected and disconnected could induce high levels of voltage on the electrodes of the bed-wetter sheet.

The purpose of the invention is therefore to provide a solution which is fail safe in connection with monitoring of a bed, and to indicate whether the bed is wet, and at the same time provides a solution which is inexpensive and simple. At the same time is requested a solution which takes personal safety and personal comfort into consideration.

SUMMARY OF THE INVENTION

According to the invention this can be achieved by designing the bed-wetter sheet so that it includes electrical connections for at least one additional point of the electrode. In this way a length of the individual electrode can be measured, and a possible failure can be found. As the electrodes are made of conductive material, the electric resistance is low, and a simple measurement of the electric resistance of the electrode will indicate whether a failure has occurred. It has the effect that it will be easy to determine whether the bed-wetter sheet has been damaged or it is fully functional.

The electrical connectors on the electrodes can be constructed in a way that a first connection of the terminal is constructed in one end of the electrode, designating a first end, and another connection of the terminal is constructed in another end of the electrode, designating the other end of the electrode. This is expedient as the whole length of the electrode in that way can be measured for failures.

An embodiment where the electrical connections are lead to more points of the electrode is particularly suitable, as it offers the opportunity of determining which part of the bed-wetter sheet has become wet, and thus—from the location of the wet spot to give an indication of which kind of human fluid it is. This means that the nursing staff becomes an indication of the kind of the problem immediately. This is particularly interesting when the patient is at home or, i.e., in a sheltered housing accommodation where the nursing staff not necessarily is within easy reach of the patient. The electrodes can hereby form a coherent long electrode with more electrically connected take off points or separate sections to be considered as individual electrodes.

The electrical connections for connecting the electrodes to the measuring circuit are terminated in plug-in connections arranged in connection with the bed-wetter sheet. This is appropriate as it will thus be possible to connect the electrodes with the measuring circuit which is to determine whether the bed-wetter sheet is wet. Furthermore, it means that the bed-wetter sheet easily can be released from lose cables after use.

In an embodiment the connectors are arranged in a joint group on the bed-wetter sheet for receiving a complementary connector mounted on a cable for connecting the electrodes with the measuring circuit. The grouping of the connectors are organized symmetrically whereby the complementary connector can be connected in more than one way, and still secure electric connection of all the conductors of the connector. In the simplest embodiment where each of at least two of the electrodes have an electric connection to each end of the electrode, there will be four connections which practically can be placed in each corner of a quadrate. As it is not important which electrode are connected to one or the other port of the measuring circuit, it will be obvious to understand that the connectors can be rotated, and therefore it can be inserted for each rotation of ninety degrees which means four correct connecting possibilities. Constructing it this way makes it easier for the nursing staff to connect the bed-wetter sheet to the measuring circuit as the connector can be assembled arbitrarily. The outlet of the cable offers the opportunity to let the cable run to one of the four sides whereby it makes the cabling to the measuring circuit easier, through a route which protects the cable against being pulled out of engagement with the electric connections of the bed-wetter sheet.

The measuring circuit is adapted to test whether the electrodes still are intact. In that electric connections from both ends of the electrodes are lead to the measuring circuit, it is possible to make a simple conduction test, a measurement of the resistance of the connection, to determine that the measuring circuit is connected to the electrodes of the bed-wetter sheet, and furthermore that these are not disconnected. In this way the basic conditions for detecting fluid on the bed-wetter sheet is secured. It is obvious that the test has to be executed on all the electric conductors making up the electrodes.

The measuring circuit is also adapted to test whether the electrodes are connected through a short circuiting. When a mistake has occurred on the bed-wetter sheet with the electrodes being short-circuited, it is important to register this, as the bed-wetter sheet in that case has to be changed with a functional bed-wetter sheet. This test also includes error testing of the cable which connects the bed-wetter sheet with the electrodes in the bed-wetter sheet and the connector, which is why eventually errors have to be searched for in the cable and in the plug-in connection.

When the bed-wetter sheet is furnished with more sub sections of the electrodes which together form an electrode, the measuring circuit is adapted to test each part section. Is it proven that the electrode is disconnected, the measuring circuit is adapted to connect more than one point at the electrode to the same measuring port. In this manner the extension of the error is minimized, and the system will still function until an appropriate occasion to change the sheet with a fully functional bed-wetter sheet occurs. Here it would be appropriate that an alarm is warning about the reduced functionality, making the service staff aware of the error. The fact that the measuring circuit is retained electrically to the electrodes at more points, gives a safer indication of the bed being wet, as a failure on the electrode in the bed-wetter sheet not necessarily makes the appliance inoperative.

To secure a safe indication of the bed being wet, the measuring circuit is adapted to perform a measurement of whether the bed-wetter sheet is wet. The measuring circuit can determine this by measuring the electric conditions between two or more electrodes. The applied measuring method could be measuring the resistance, the capacity or the impedance between the electrodes. The measurements could in practise be carried out regularly to achieve an appropriate compromise between current consumption and a punctual indication of a wet bed. Furthermore, the sensitivity of the measuring circuit has to be adapted to carry out measurements indicating the presence of fluid containing conductive ions in a concentration as known from human fluids.

In order to secure a safe indication of whether the bed is wet, the measuring circuit regularly has to change between a first function, comprising testing of all the conductors in the electrodes being intact and unbroken, and a second function, comprising a measurement to determine whether the bed is wet.

The measuring circuit can be mounted in its own housing completed with power supply, and an alarm function. In case of an adjustable bed, comprising an actuator system and a control, it would be appropriate that the control furthermore comprises the measuring circuit for connection of a bed-wetter sheet, as an alarm indicating a wet bed can be transmitted via the connection of the bed to the surroundings, or be represented directly in the bed on the operating panel. Similarly an alarm from a separate system for indication of a wet bed can be transmitted to a control for an adjustable bed, and hereby become a constituent part of the information which is communicated from the actuator system.

In order to obtain higher personal safety, the measuring circuit is separated galvanically from the control in that the supply of energy takes place inductively. The coupling which a person in the bed has to the mains is hereby galvanically separated in two links, in the first link by the transformer which supplies the actuator system with power from the mains, and in a second link of an inductive coupling furnished to supply only a limited quantity of energy to the measuring circuit, and to the bed-wetter sheet. In that the signal transmission between the control and the measuring circuit is performed optically by optocouplers potential errors are eliminated.

BRIEF DESCRIPTION OF THE DRAWINGS

An embodiment according to the invention will be described more detailed below with reference to the accompanying drawings, in which.

DETAILED DESCRIPTION OF THE PREFERRED EMBODIMENT

Figure 1:
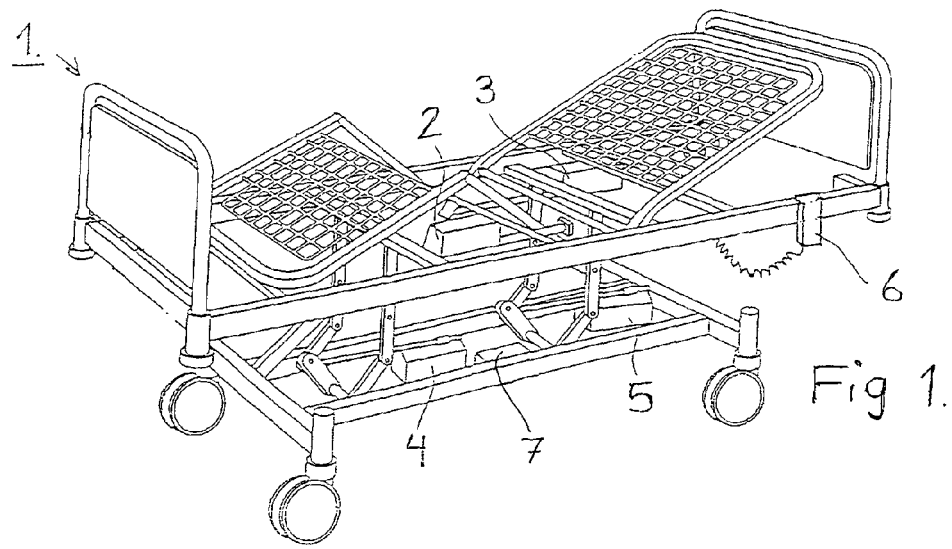
FIG. 1 shows an adjustable bed.

FIG. 1 in the drawing shows an adjustable bed 1 furnished with a motor drive in the form of linear electrically driven actuators 2, 3, 4, 5 for adjustment of the resting shape and the height of the bed. Linear electrically-driven actuators are well known from EP 531 247 A1, EP 586 326 A1, EP 647 799 and EP 662 573 A1 (all of them LINAK A/S) on which the construction and the functionality of an electrically-driven linear actuator is explained. The actuators of the adjustable bed are operated on an operation panel 6, which like the electrically-driven actuators 2, 3, 4, 5, is connected with a control 7. The control 7 is connected with a power supply supplying electric energy for operating the control and the electrically driven actuators 2, 3, 4, 5. The electrically-driven actuators 2, 3, 4, 5 are likewise connected to the control in that they are connected with a cable furnished with a plug-in connector. The control 7 is likewise furnished with ports for connecting various types of equipment for the actuator system in which the ports are adapted to receive a signal from a connected equipment about an event which has occurred. The signal can simply be generated in that the contact points of the port are short-circuited. In another embodiment the port is adapted to receive a signal in the form of a voltage or current.

Figure 2:
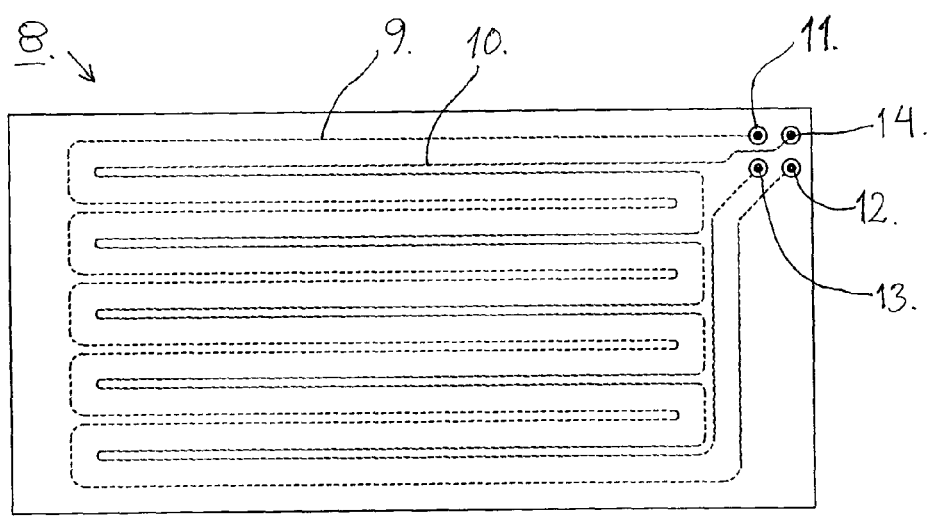
FIG. 2 shows a bed-wetter sheet indicating the position of the electrodes and of the electric connections.

In yet another embodiment the port is particularly adapted for connecting a bed-wetter sheet 8, as shown in FIG. 2. The bed-wetter sheet 8 is used in the bed 1 for indicating that the bed is wet, in order to warn the nursing staff that assistance is needed. The bed-wetter sheet 8 is constructed as a bottom sheet in the bed and furnished with two electrodes 9, 10 which are arranged in the bed-wetter sheet 8 in a labyrinth-shaped pattern. Each electrode 9, 10 in the bed-wetter sheet is furnished with a connector 11, 12; 13, 14 at both ends. Hereby, the section can be measured through in order to control that the electrode 9, 10 is intact and unbroken. The control 7 is adapted to test whether a connected bed-wetter sheet 8 is fully functional by performing a simple conducting test between the two connectors 11, 12; 13, 14 to each electrode 9, 10. When the bed-wetter sheet 8 has been tested and confirmed to be fully functionally, the control 7 enters into another state in which the ports function as a measuring circuit to measure the conductivity between the two electrodes 9, 10. In the normal state in which the bed-wetter sheet 8 is dry, the electric isolation between the electrodes 9, 10 is high. If the bed-wetter sheet becomes wet from human fluid containing salt, the electric isolation between the electrodes 9, 10 is broken, and thus an electric current can run from one to another electrode 9, 10. When the electricity exceeds a threshold value, an alarm signals that a situation has occurred whereby the bed has become wet. During operation the control 7 is set up to run through a sequence which as a first action measures that the electrodes 9, 10 of the bed-wetter sheet 8 are intact and functionally, and as a second action measures if there is a direct short circuiting or higher conductivity (a bed wetting) between the electrodes 9, 10, and then in a third and last state becomes inactive. The duration of the two measuring states is kept short to save energy. The resting state in which the measuring circuit is inactive is therefore relatively long seen in relation to the whole sequence, but has to be determined from a suitable compromise dependent on how fast the indication of a wet bed should be given after the incident has occurred.

Figure 3:
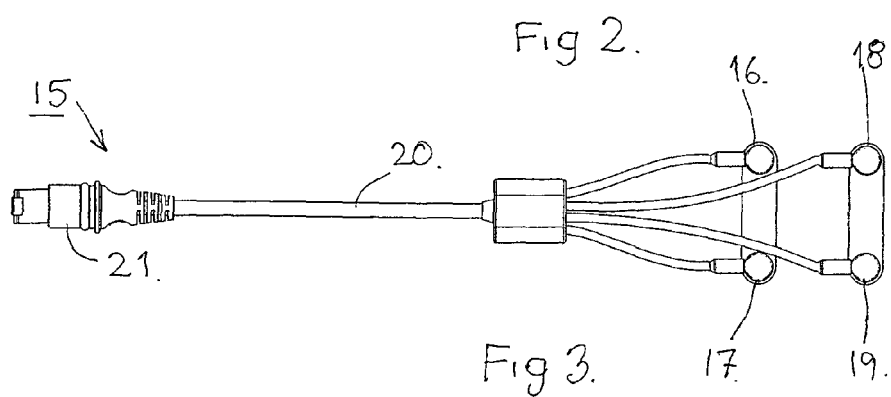
FIG. 3 shows a cable for electric connection of a bed-wetter sheet with a measuring circuit.

As shown in FIG. 2, the electric connectors 11, 12, 13, 14 in the bed-wetter sheet 8 are arranged in a square pattern. A similar arrangement for a cable 15 is shown in FIG. 3 where the connectors 16, 17, 18, 19 are gathered two by two with a distance piece, however, a device in which the four connections 16, 17, 18, 19 are mounted in a quadrate would also be an appropriate arrangement. As the arrangement of the connectors 11, 12, 13, 14 on the bed-wetter sheet 8, and the connectors 16, 17, 18, 19 on the cable 15 are mounted quadratically, the two parts can be connected in four different ways, all of which being able to support the functioning of the bed-wetter sheet 8. This is achieved in that the two electric connectors 11, 12; 13, 14 of the electrodes 9, 10 as shown in FIG. 2 have been mounted hundred and eighty degrees (half a rotation) displaced to each other, around a centre point in the connection area. This makes the mounting of the cable 15 on the bed-wetter sheet 8 particularly simple as there is no particularly considerations to be taken regarding coding the coupling in a certain manner. Furthermore, it gives the advantage that the coupling of the electric connectors 11, 12; 13, 14 in the bed-wetter sheet and the electrical connectors 16, 17, 18, 19 on the cable can be made in a manner in which the wire part 20 of the cable can be directed most practically for connecting the bed-wetter sheet 8 to the control 7. For instance a wire routing protecting the cable 15 better against being pulled out of its connection to the bed-wetter sheet 8 could be chosen, or a wire routing intending that the cable 15 is not being damaged by movable parts when adjusting the bed.

The reason for the electrical connection terminals 11, 12, 13, 14 here being quadratically arranged on the bed-wetter sheet is due to their numbers. A number of for example twelve connections may likewise be constructed symmetrically supporting the cable being connected in an arbitrary angle in relation to the electric connector in the bed-wetter sheet.

Furthermore, the electrical connector 11, 12, 13, 14 constitute concurrent connections with the electrical connectors 16, 17, 18, 19 on the cable 15. A particular suitable type is shaped as a snap fastener known from clothes. The other end of the cable is 15 is furnished with a plug 21 of the Multifit type which fits into the socket of a port in the control 7.

Figure 4:
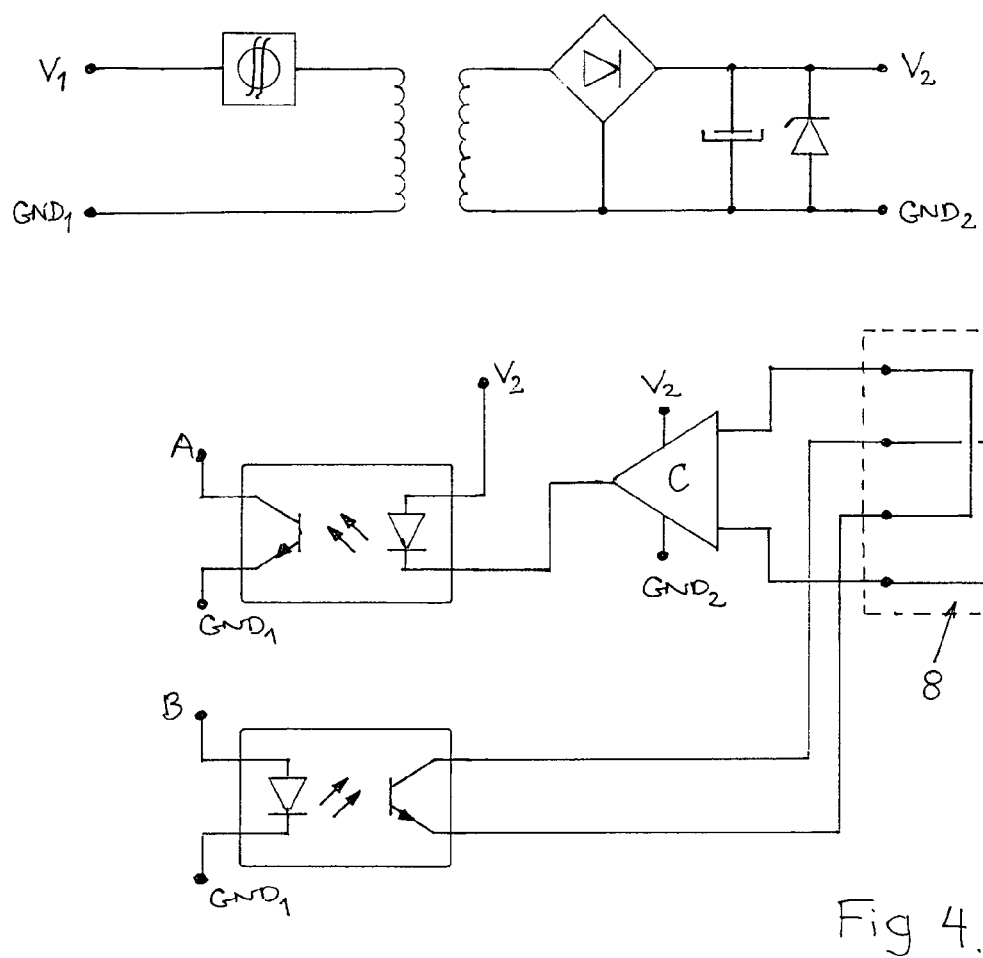
FIG. 4 shows a basic circuit diagram for a galvanically separated electric measuring circuit.

A particularly suitable embodiment of the principle diagram of the measuring circuit is shown in FIG. 4. Such a construction is excellent in that the bed-wetter sheet and the measuring circuit are galvanically separated from the actuator system, which means that the personal safety for avoiding electrical chock is high. The supply voltage to the measuring circuit is taken from the power supply of the actuator system which already is separated galvanically from the current network being transmitted through a first transformer. The supply of the measuring circuit comes from yet another inductive coupling, furnished with an oscillator supplying a primary coil with energy which again via an inductive coupling for yet another coil supplies energy to be taken from the last coil, being a secondary coil. The electric energy to be tapped from the secondary coil is a pulsing electric voltage rectified and smoothened in order to supply the measuring circuit. The personal safety is especially secured in that the supply of energy to be conveyed via the inductive coil being so small that a situation compromising the personal safety never will occur. The zenerdiode which is switched parallel to the smoothing capacitor likewise prevents accumulation of a high voltage over the capacitor whereby its energy is kept low. Simultaneously, the signal routes to and from the measuring circuit are furnished with galvanically separation in the form of optocouplers which is why a potential error in the control never would cause a fault current being potential dangerous for human beings. The energy being at disposal in the measuring circuit solely comes from the inductive coupling. The signalling to and from the measuring circuit comprises one input and one output. When input, here being marked B, is activated the transistor of the optocoupler is functioning as a short circuiting on the two connections for the bed-wetter sheet, which are conducted to the end terminations of the two electrodes. This indicates that two electrodes are serially connected via optocouplers, and would in fact be short-circuited in the same manner as by a bed-wetting. The measuring circuit with its measuring amplifier C will catch this, and will signal this to point A via an optocoupler, being an output for advising a bed-wetting to the control. When the control impresses operative voltage to input B, it is to be expected that output A is active. If this does not happen, the control may conclude that the bed-wetter sheet has been disconnected, or a breakage on one of the electrodes has occurred. The control may therefore indicate this to the staff having to solve the problem. Of course the possibility exists that the bed-wetter sheet still has limited functionality if the breakage has occurred in one of the electrodes of the bed-wetter sheet. The measuring circuit may therefore when operating, carry out a routine, shifting between testing the intactness of the electrodes and the connections, and afterwards testing for short circuiting between the electrodes. The testing and the measuring intervals can periodically be carried out in short time i.e. periods of a fraction of a second. Dependent of how fast one wish to be updated about a bed-wetting a pause can be inserted at the period of time at which the measuring circuit enters into its resting state. The pause interval can be extremely long, i.e. some minutes. The testing, measuring, and the pause functionality as described, and the time intervals thereof are operated from a microprocessor in the control which is furnished with portions of program codes for performance of the functionality.

The invention claimed is:

1. An apparatus for indicating whether a bed is wet, said apparatus comprising:
    a sheet with first and second electrodes, said the first and second electrodes each comprising electrically conductive material, and the first and second electrodes being located at a distance from each other in or at the sheet,
    a measuring circuit for measuring at least one of resistance, capacitance and impedance between the first and second electrodes,
    each of said first and second electrodes including respective first and second ends thereof, each of said first and second electrodes further including respective first and second electrical connection points at said respective first and second ends of said first and second electrodes, wherein said first and second electrical connection points for each of said first and second electrodes are configured for electrical connection to said measuring circuit, and
    a control unit for determining whether the bed is wet on the basis of the measurements from the measuring circuit.

2. The apparatus according to claim 1, wherein the respective first and second electric connection points are connected to the respective electrode at spots that divide the respective electrode into segments or sub areas of the sheet.

3. The apparatus according to claim 1, wherein the first and second electric connection points for connecting the respective electrodes to the measuring circuit are terminated in connectors arranged in connection to the sheet.

4. The apparatus according to claim 3, wherein the first and second connectors of the first and second electrodes are arranged in a symmetrical pattern around a centre point in an area of the connection point on the sheet.

5. The apparatus according to claim 1, wherein the measuring circuit is constructed to perform a test whether the first and second electrodes are intact.

6. The apparatus according to claim 1, wherein the measuring circuit is constructed to test whether the first and second electrodes are interconnected due to short circuiting.

7. The apparatus according to claim 1, wherein the measuring circuit is constructed to connect more than one point at the electrode to the same measuring port when it is proven that at least one of the electrodes are disconnected.

8. The apparatus of claim 1, wherein said control unit is configured to determine whether said first and second electrodes are intact and unbroken by performing a conductivity test (i) between said first and second electrical connection points of said first electrode, (ii) between the first and second electrical connection points of said second electrode, and (iii) on said first and second electrodes electrically connected in a series relationship.

9. The apparatus of claim 8 wherein said measurement comprises an electric current between said first and second electrodes, and wherein said control unit is configured to determine that said bed is wet when said electric current exceeds a threshold value.

10. The apparatus of claim 9 wherein an alarm is signaled when the control unit has determined that said bed is wet.

11. The apparatus of claim 1 wherein said first electrode extends along a first path between said first and second ends of said first electrode, and wherein said second electrode extends along a second path between said first and second ends of said second electrode, wherein said first and second electrodes are disposed on a member that exhibits high electrical isolation between said first and second electrodes when said member is dry.

12. The apparatus of claim 11 wherein said first and second paths associated with said first and second electrodes are arranged in labyrinth shaped pattern.

13. A method for measuring whether a sheet is wet using first and second electrically-conductive electrodes in or at the sheet wherein each of said first and second electrodes includes respective first and second electrical connection points at respective first and second ends thereof, said method comprising:
    i) a first action, after activation by a user, of determining whether said first and second electrodes are complete and intact by performing one of (i) a conductivity test between said first and second electrical connection points of said first electrode; (ii) a conductivity test between said first and second electrical connection points of said second electrode; and (iii) a conductivity test through said first and second electrodes electrically connected in a series relationship,
    ii) a second action of testing whether isolation between the electrodes are sufficient, and accordingly indicating an error in the sheet or a bed-wetting at the sheet, and
    iii) a third action of bringing the measuring circuit to a resting state in a fixed period of time, and after the termination of the period of time continuously repeating steps i)-iii) until either a user operated disconnection, or a bed-wetting happens, whereby a bed-wetting releases an alarm for advising a service staff that a cleaning task has to be done.

* * * * *